United States Patent
Liu

(10) Patent No.: US 9,932,624 B2
(45) Date of Patent: *Apr. 3, 2018

(54) METHOD FOR RECOVERING SPERM NUCLEIC ACID FROM A FORENSIC SAMPLE

(71) Applicant: LIFE TECHNOLOGIES CORPORATION, Carlsbad, CA (US)

(72) Inventor: Jason Yingjie Liu, Foster City, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/612,183

(22) Filed: Feb. 2, 2015

(65) Prior Publication Data

US 2015/0211051 A1    Jul. 30, 2015

Related U.S. Application Data

(63) Continuation of application No. 12/177,579, filed on Jul. 22, 2008, now Pat. No. 8,969,044.

(60) Provisional application No. 60/961,734, filed on Jul. 23, 2007.

(51) Int. Cl.
    *C12P 19/34*    (2006.01)
    *C12Q 1/68*     (2018.01)
    *C12N 15/10*    (2006.01)

(52) U.S. Cl.
    CPC ....... *C12Q 1/6806* (2013.01); *C12N 15/1003* (2013.01)

(58) Field of Classification Search
    None
    See application file for complete search history.

(56) References Cited

U.S. PATENT DOCUMENTS

| | | | |
|---|---|---|---|
| 5,234,809 A | 8/1993 | Boom et al. | |
| 5,523,231 A | 6/1996 | Reeve et al. | |
| 5,541,072 A | 7/1996 | Wang et al. | |
| 5,705,628 A | 1/1998 | Hawkins | |
| 6,368,800 B1 | 4/2002 | Smith et al. | |
| 6,855,499 B1 | 2/2005 | Nargessi | |
| 7,320,891 B2 | 1/2008 | Tereba et al. | |
| 7,919,436 B2 * | 4/2011 | Frutos ............ | C12Q 1/689 435/259 |
| 2002/0151089 A1 | 10/2002 | Chapman et al. | |
| 2002/0182751 A1 * | 12/2002 | Herr ............... | C07K 16/18 436/526 |
| 2003/0038087 A1 | 2/2003 | Garvin | |
| 2003/0215845 A1 * | 11/2003 | Bille .............. | C12N 1/06 435/6.12 |
| 2005/0019905 A1 | 1/2005 | Larson et al. | |
| 2005/0032097 A1 | 2/2005 | Garvin | |
| 2005/0064575 A1 | 3/2005 | Belgrader et al. | |
| 2006/0141512 A1 * | 6/2006 | Sinha ............... | C12Q 1/6806 435/6.16 |
| 2008/0176320 A1 | 7/2008 | Liu | |
| 2008/0206771 A1 | 8/2008 | Liu | |
| 2008/0261293 A1 | 10/2008 | Garvin | |
| 2008/0281089 A1 | 11/2008 | Liu | |

FOREIGN PATENT DOCUMENTS

| | | |
|---|---|---|
| WO | 2001035759 | 5/2001 |
| WO | 2001052968 | 7/2001 |
| WO | 2003070898 | 8/2003 |
| WO | 2006031591 | 3/2006 |
| WO | 2008089280 | 7/2008 |

OTHER PUBLICATIONS

Chen, et al, "A Physical Method for Separating Spermatozoa from Epithelial Cells in Sexual Assault Evidence". J. Forensic Science 43: 1998, pp. 114-118.
EZ1 DNA Handbook, Second Edition, Feb. 2004, 24 pages, www.giagen.com.
Garvin, A. M. "Filtration Based DNA Preparation for Sexual Assault Cases", Journal of Forensic Sciences, vol. 48, No. 5, 2003, pp. 1084-1087.
Gill, et al, "Forensic application of DNA 'fingerprints'". Nature 318: 1985, pp. 577-579.
Giusti, et al, "Application of Deoxyribonucleic Acid (DNA) Polymorphisms to the Analysis of DNA Recovered from Sperm". J. Forensic Sci. 31: 1986, pp. 409-417.
Horsman, PhD Dissertation, May 2007.
Horsman, et al, 2005. "Separation of Sperm and Endothelial Cells in a Microfabricated Device: Potential Application to Forensic Analysis of Sexual Assault Evidence". Anal. Chem 77(3): 742-749.
Iida & Kishi, Identification, characterization and forensic application of novel Y-STRs, Legal Medicine, vol. 7, 2005, pp. 255-258.
Maxwell® 16 datasheet, Profiled in DNA, Feb. 2006, www.promega.com, 3 pages.
Maxwell® 16 System datasheet, www.promega.com/maxwell1116/dnaiq/, 4 pages, Nov. 15, 2016.
Tsukada, K. et al., Sperm DNA extraction from mixed stains using the Differex™ System, International Congress Series, vol. 1288, 2006, pp. 700-703.
Westbrook, "Differential nuclear localization of the cancerltestis-associated protein, SPAN-XICTp11, in transfected cells and in 50% of Human Spematozoa", Biology of Reproduction; vol. 64, 2001, pp. 345-358.
Wiegand, et al., "DNA extraction from mixtures of body fluid using mild preferential lysis". Int J. Leg Med. 104: 1992, pp. 359-360.
Yoshida, et al "The modified method of two-step differential extraction of sperm and vaginal epithelial cell DNA from vaginal fluid mixed with semen", Forensic Sci. Int. 72: 1995, pp. 25-33.

* cited by examiner

*Primary Examiner* — Catherine S Hibbert

(57) ABSTRACT

A method for selectively recovering nucleic acid from a sperm cell in a sample containing cells of at least a sperm cell and an epithelial cell, and a cell suspension medium comprising extracellular impurities, is provided. The method entails introducing a sample into a vessel, sequestering the cells from the remaining sample components, washing the cells with a washing solution either before or after sequestration, removing the impurities-containing cell suspension medium from the vessel while retaining the cells; lysing selectively cells of the first cell type; and isolating the nucleic acid from the lysed cells. Methods for recovering nucleic acid from the second cell type are also provided.

17 Claims, 10 Drawing Sheets

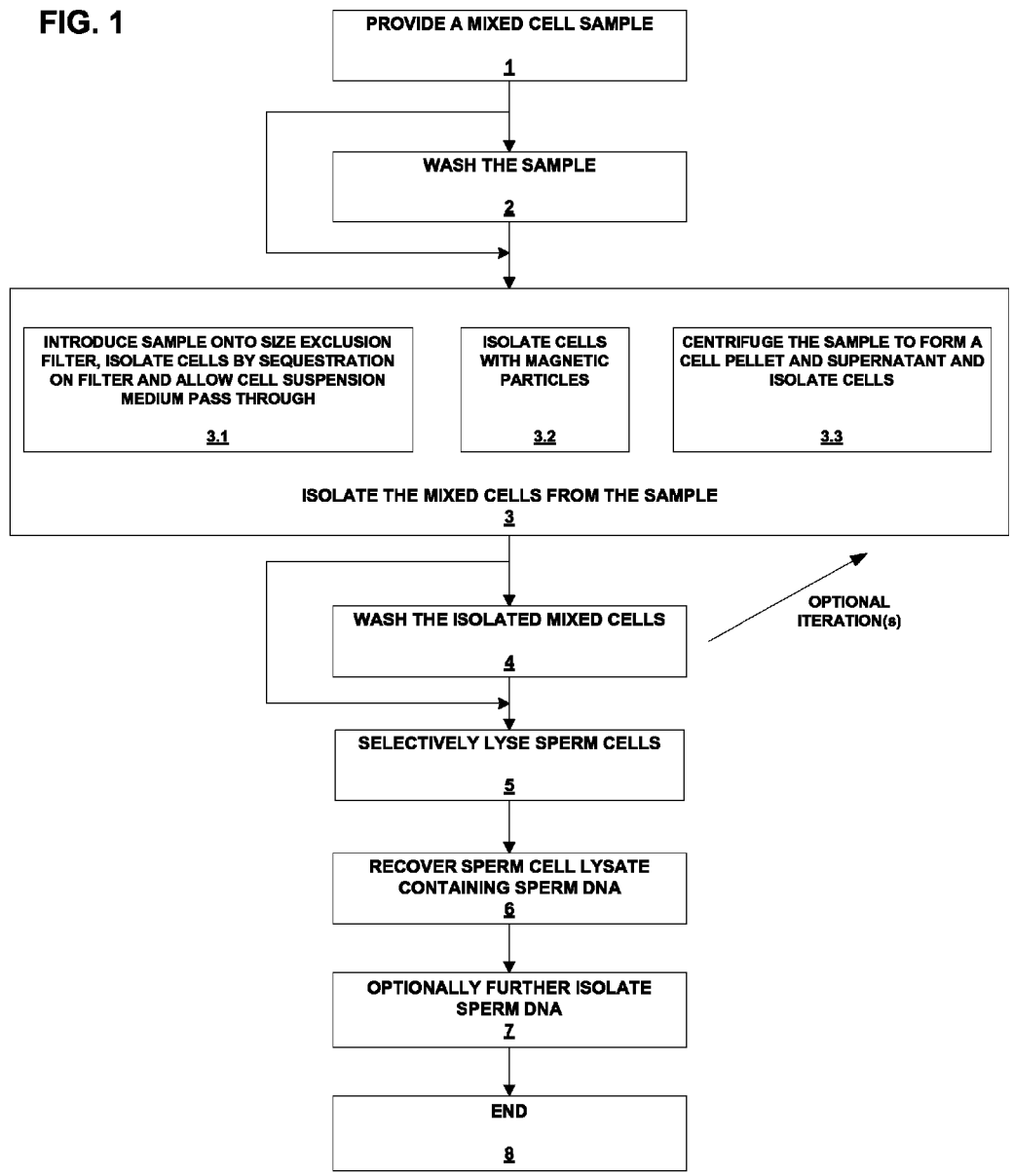

METHOD FOR RECOVERING SPERM NUCLEIC ACID FROM A FORENSIC SAMPLE

RELATED APPLICATION

Figure 2A:
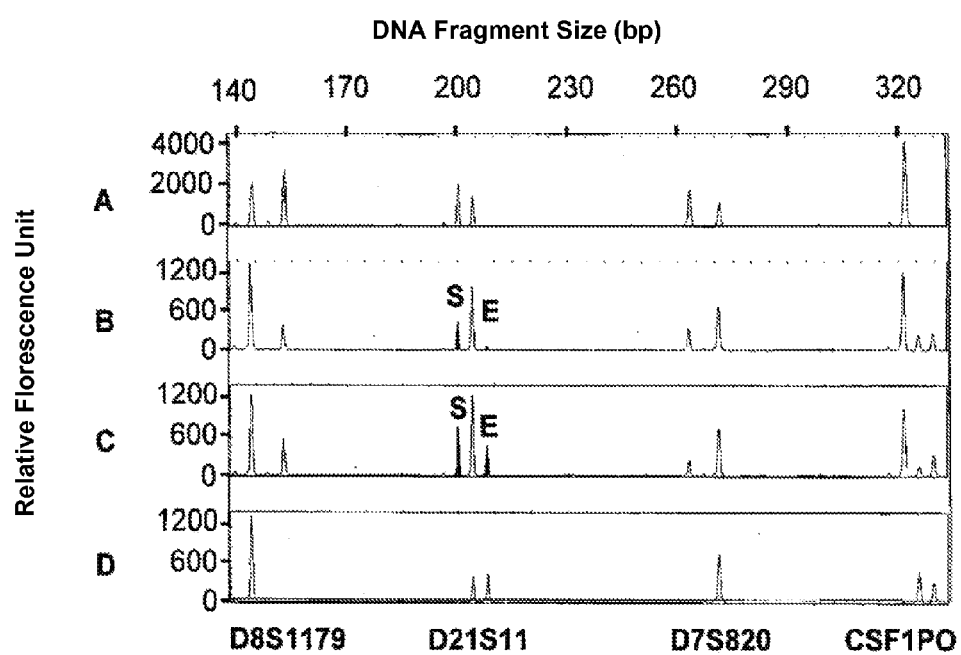
Figure 2B:
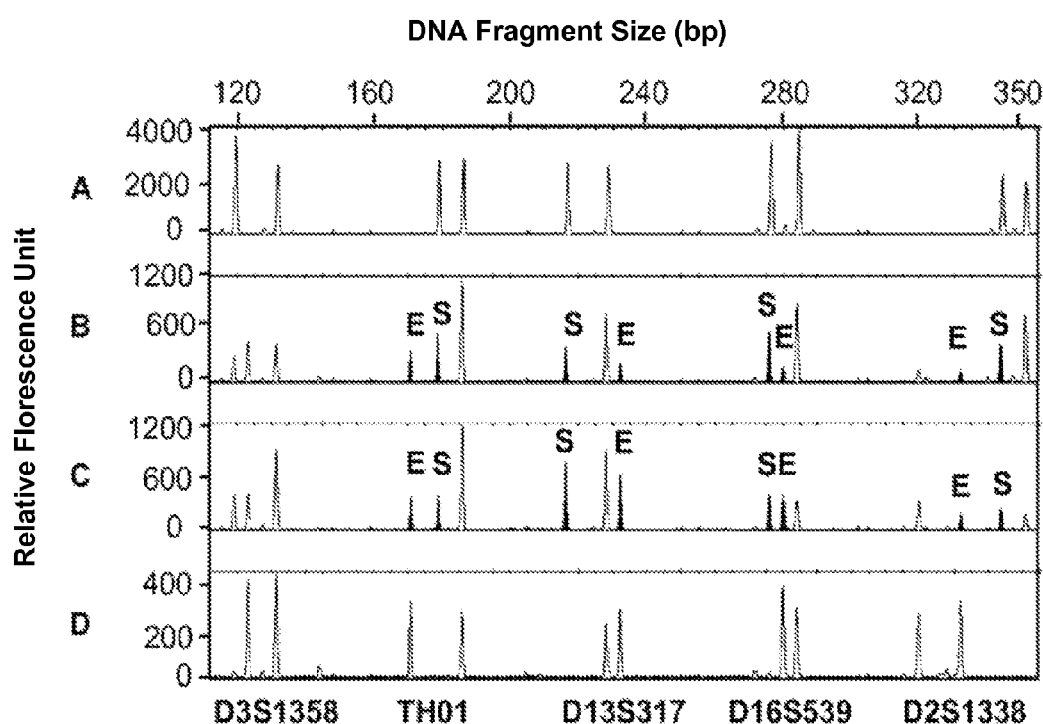
Figure 2C:
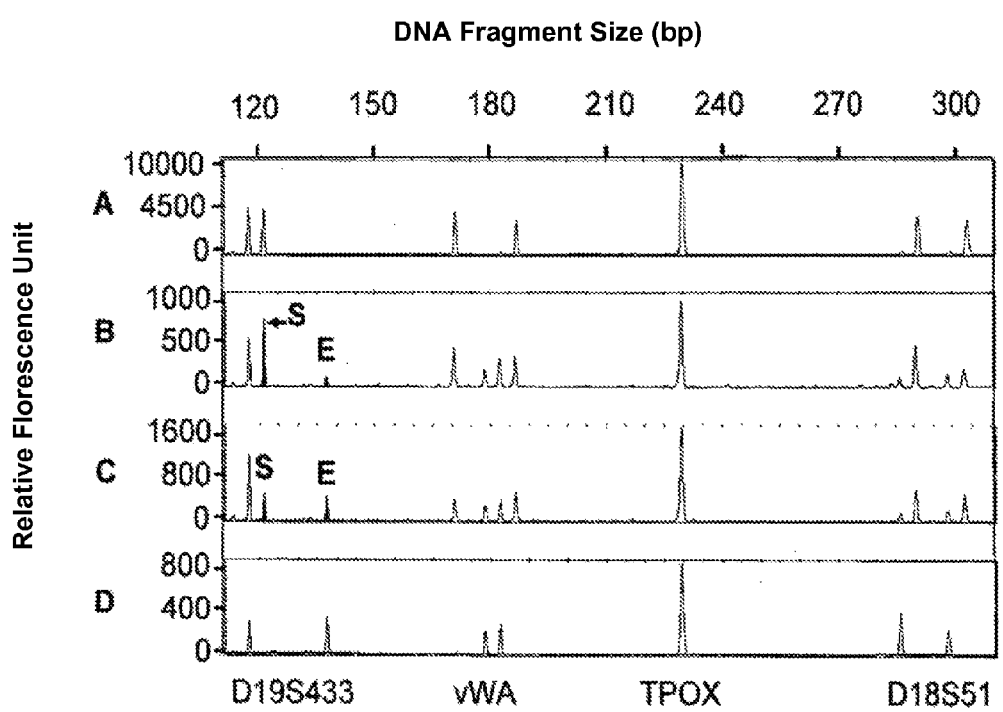

This application claims priority under 35 U.S.C. § 119(e) to U.S. Provisional Application No. 60/961,734, filed Jul. 23, 2007.

FIELD OF THE INVENTION

The invention relates to the field of isolating cells from a sample containing cells and non-cell impurities and further isolating nucleic acid from a specific cell type.

More specifically, the invention relates to the field of isolating sperm cells from a sample containing extracellular impurities and at least one other type of contaminating cell (e.g., epithelial cell) and recovering DNA from the sperm cells and nonsperm cells for various purposes, including forensic purposes.

BACKGROUND OF THE INVENTION

Forensic DNA analysis of sexual assault evidence often involves analysis of DNA from sperm cells and DNA from other cells such as epithelial cells. Sperm cells are normally obtained from a rape victim by rubbing a swab against a mucous membrane. The samples obtained from victims often contain a mixture of sperm and epithelial cells. Because the epithelial cells may outnumber sperm cells in the sample by at least an order of magnitude, the former can cause contamination of sperm cell DNA, when sperm DNA is purified. Consequently, it is often desirable to separate, as cleanly as possible, the sperm cells and epithelial cells, or the sperm DNA and the epithelial DNA, prior to analysis. Separation and isolation of DNA from sperm and epithelial cells are essential steps in identifying an assailant from a forensic specimen, and in associating the assailant with the victim.

The standard method for purifying sperm from swabs is based on differential extraction. Separation of the sperm DNA from the victim's DNA removes ambiguity, facilitates DNA analysis and allows for easier interpretation of the assailant's DNA profile in a rape case. Although differential extraction is commonly used to separate sperm and epithelial cells, the standard protocol is time consuming and laborious, and entails epithelial cell lysis prior to sperm cell lysis.

Typically, cells are first resuspended from a forensic specimen, followed by selective digestion of the victim's epithelial cells with a solution containing Proteinase K and SDS (sodium dodecyl sulfate). The intact sperm are separated from the solubilized, contaminating DNA and epithelial cell debris by centrifugation, careful removal of supernatant, and extensive washing of the sperm pellet (see e.g., Giusti et al., J. Forensic Sci., 31:409-417, 1986; Gill et al. Nature 318:577-579, 1985; Wiegand et al., Int J. Legal Med., 104:359-360, 1992; and Yoshida et al., Forensic Sci. Int., 72:25-33, 1995). Unfortunately, the processes of centrifugation and careful removal of supernatant are difficult to automate and can cause the loss of sperm DNA due to multiple sample handling steps.

In one example of this procedure, Gill et al. (supra) describe a process for isolating sperm DNA from vaginal swabs taken from sexual assault victims. These swabs contain sperm and also a large excess of the victim's epithelial cells. The epithelial cells and the DNA contained in these cells are removed by preferential lysis (i.e., by incubation of the cell mixture in a buffer solution containing SDS, and Proteinase K). Sperm nuclei are impervious to this treatment because they have disulfide bond cross-linked thiol-rich proteins, while other cell types are digested and the corresponding DNA is solubilized. After preferential lysis, the samples are centrifuged to separate the sperm nuclei from the victim's solubilized DNA. The supernatant containing the victim's DNA is removed and the sperm pellet is washed repeatedly. The sperm nuclei are subsequently lysed by treatment with a buffer solution containing SDS, proteinase K and DTT (dithiothreitol), and the lysate separated from the contaminating cells by centrifugation.

Wiegand et al. (supra) attempted to improve on the method of Gill et al. for samples having low sperm counts by using mild lysis conditions and by avoiding the washing steps.

A number of proposals for separating sperm cells from epithelial cells are based on filtration. Chen et al. (J Forensic Science 43:114-118, 1998) and Garvin (PCT/US01/01835) separate the sperm from the epithelial cells before differential lysis by gravitational or mild vacuum filtration or by use of a filter material that can withstand strong vacuum or centrifugal forces without having the pores increase in size. DNA is then isolated from the sperm collected in the filtrate.

Differential extraction, specifically for sperm cell analysis, has been carried out by first lysing epithelial cells, before extracting the DNA from sperm. In order to reduce the time for forensic analysis, it is desirable to selectively extract the DNA from the sperm cells, initially. In addition, because the selective epithelial cell lysis conditions also cause some sperm lysis, lysing epithelial cells before the sperm cell fraction reduces the number of sperm cells present in the sample. The additional wash steps that are required to remove epithelial DNA also contribute to the loss of sperm cells.

Accurate sperm analysis can be impeded by the lysing or presence of epithelial cells, or other contaminating cell types, such as leukocytes. DNA present in the forensic sample, from damaged nonsperm cells, can contaminate the cells (most likely by binding to the surface of sperm cells), which can inhibit accurate identification of a perpetrator, especially when the number of recovered sperm cells is low.

The present inventor discovered that although techniques exist for differential extraction of one type of nucleic acid (from an individual cell type) from a heterogeneous cell population, residual contaminating nucleic acid is still a problem that warrants more precise extraction methodologies. One application where the need exists for highly specific differential extraction is forensic, specifically sexual assault analysis.

Because of their fragile nature, epithelial and other cells, e.g., leukocytes, in a sexual assault sample often break and lyse during handling, sample processing or storage. This residual DNA, if not removed, may contaminate male DNA during selective sperm lysis, especially when the number of sperm cells is low. In addition, epithelial and sperm cell surfaces are highly functionalized, with molecules (e.g., glycoproteins) that bind nucleic acid through ionic interactions, as well as other non-covalent methods. These cell surface proteins have been found to associate with extracellular nucleic acid present in a sample.

SUMMARY OF THE INVENTION

The present invention serves to reduce the amount of residual DNA and contaminating cells, e.g., leukocytes, present in a forensic sample, by implementation of a novel wash step, prior to sperm cell lysis.

The present invention can be employed with classical centrifugation based methods, size exclusion filtration, in addition to particle- or bead-based methodologies for isolating cells from a sample. The methodology is readily adaptable to automation and high throughput with existing equipment such as the Beckman Biomek® (Beckman Coulter, Fullerton, Calif.) or a Tecan liquid automated handling system (e.g., Freedom Evo® Services Tecan Systems, San Jose, Calif.). The invention is more widely applicable to both forensic and other situations where nucleic acid has to be isolated from one type of cell found in a mixture of more than one type of cell, as long as each cell type can be selectively lysed (except the last remaining cell type which need not be selectively lysed).

The present invention, in one aspect, concerns a method for selectively recovering DNA from sperm cells in a sample containing mixed sperm cells and epithelial cells and a cell suspension medium comprising impurities. The impurities include contaminating residual DNA and other contaminating cells that may be present, such as leukocytes. In this aspect, the method entails isolating the mixed cells from the medium, in a first isolating step, lysing selectively the sperm cells, and recovering the DNA from the sperm cells. The method also includes at least one of two additional steps, wherein the first step is a sample wash with a first washing solution that disengages or digests residual DNA from the surface of the cells prior to the first isolating step. The second step includes a wash/isolating procedure that comprises washing the isolated mixed cells with a second washing solution followed by the isolation of the washed mixed cells from the second washing solution in a second isolating step, prior to the lysing step. The first or second washing solution selectively lyses leukocytes, if leukocytes are present in the sample. It should be noted that since the second isolating step might not be performed (in the event there is no wash step after the first isolating step) there could be only one isolating step in the process.

The present inventor found that this simple wash or washes effectively reduces the problem of residual DNA contamination such that it will not interfere with genotyping without resorting to expensive, or time consuming or manipulative steps that could introduce other problems.

In a further aspect, the cells are isolated by either size exclusion filtration, by centrifugation, or with magnetic particles.

In another aspect, a method is provided for selectively recovering DNA from sperm cells in a sample containing mixed sperm cells and epithelial cells and a cell suspension medium comprising impurities, wherein the impurities include contaminating extracellular material such as residual DNA and possibly other contaminating cells such as leukocytes. The method entails introducing the sample onto a size exclusion filter, including any first washing solution, isolating the mixed cells from the cell suspension medium, in a first isolating step, by sequestering the cells on the filter and allowing the cell suspension medium to form a filtrate, lysing selectively the sperm cells, and recovering the DNA from the sperm cells. The method also includes at least one of two additional steps, wherein the first step is a sample wash that includes washing the sample by mixing it with a first washing solution to form a washed sample, prior to introducing the sample onto the size exclusion filter. The second step includes a wash/isolating procedure that comprises washing the isolated mixed cells with a second washing solution followed by the isolation of the washed mixed cells from the second washing solution in a second isolating step, prior to the lysing step. The first or second washing solution serves as a selective leukocyte lysis buffer, if leukocytes are present in the sample.

In yet another aspect of the invention, a method for selectively recovering nucleic acid from sperm cells in a sample containing mixed sperm cells and epithelial cells and a cell suspension medium comprising impurities is provided. The impurities include contaminating residual DNA and possibly other contaminating cells such as leukocytes. The method entails centrifuging the sample, including any first washing solution, to form a cell pellet and a supernatant containing the suspension medium, including any first washing solution, thereby sequestering the mixed cells from the suspension, followed by isolating the mixed cells from the supernatant in a first isolating step, lysing selectively the sperm cells; and recovering DNA from the sperm cells. The method also includes at least one of two additional steps wherein the first step is a sample wash step that comprises mixing the sample with a first washing solution to form a washed sample. The second step is a wash/isolation procedure and comprises washing the isolated mixed cells with a second washing solution followed by centrifuging the washed mixed cells and second washing solution to form a pellet and a supernatant, thereby sequestering the washed cells from the suspension, followed by isolating the mixed washed cells from the supernatant, in a second isolating step, prior to said lysing step. The first or second washing solution can selectively lyse leukocytes, if leukocytes are present in the sample.

In one aspect, the first washing solution or the second washing solution or both washing solutions independently comprise one or a combination of cationic salt such as $MgCl_2$, NaCl, KCl; polycation such as poly-lysine, polyanion such as heparin, all of which can interfere with DNA-cell surface interaction. Salt solution such as $MgCl_2$ can also lyse leukocytes by imposing osmotic pressure, or disrupting leukocyte membrane and chromatin structure. In various aspects, DNase, which can digest extraneous DNA, is employed as a wash solution or portion thereof.

In a particular aspect of the invention, the sample comprises a forensic specimen, which can include a specimen taken from a sexual assault victim. The cell types in such a sample include at least sperm and epithelial cells and sometimes leukocytes as well. In principle, the nucleic acid in a sample can be DNA or mRNA or total RNA. Commonly, it is DNA.

In another aspect of the invention, the isolated sperm nucleic acid can be used for downstream steps, including, but not limited to, quantifying the purified nucleic acid, amplifying the nucleic acid and separating the amplified short tandem repeat fragments for genotyping.

DRAWINGS

The skilled artisan will understand that the drawings, described below, are for illustration purposes only. The drawings are not intended to limit the scope of the present invention in any way.

FIG. 1 is a process flow chart showing steps to isolate and recover DNA from sperm cells in a sample containing both sperm and epithelial cells, in accordance with some embodiments of the present invention.

Figure 2D:
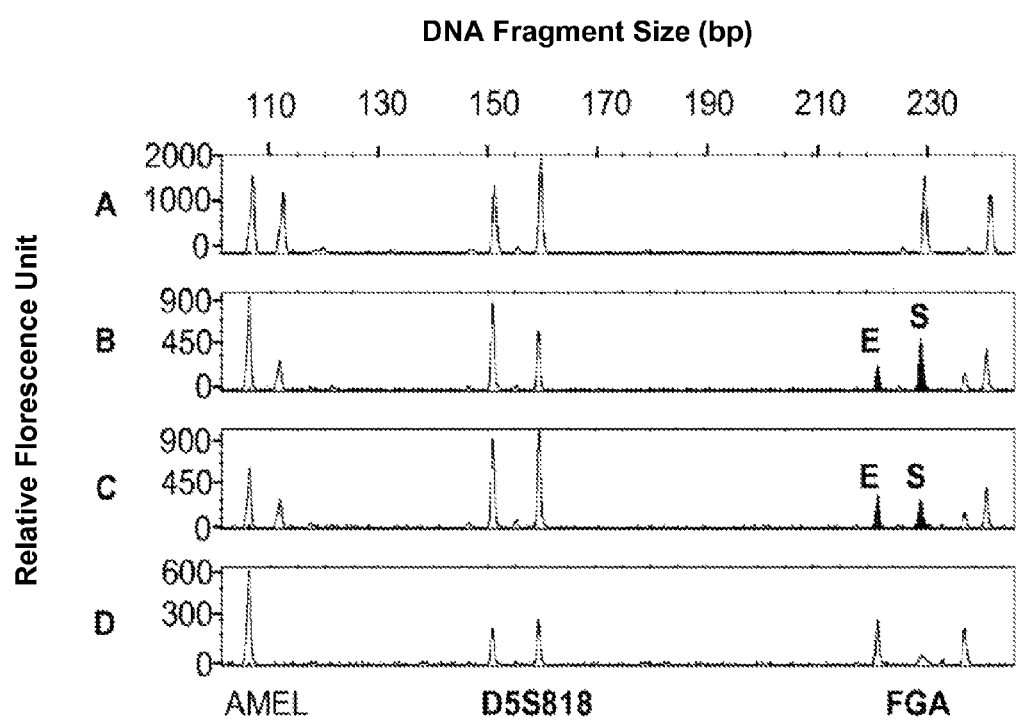

FIGS. 2A-2D are STR typing profiles of sperm DNA isolated with a method of the invention as illustrated in Example 1. Primers for the various loci were labeled with a fluorescent dye, followed by amplification of the various loci and separation of products by electrophoresis. Fluorescence excitation/emission wavelengths and dyes employed were 494/522 nm, 6-FAM (FIG. 2A), 538/554 nm, VIC (FIG. 2B), 546/575 nm, NED (FIG. 2C), 558/595 nm, PET (FIG. 2D).

Figure 3:
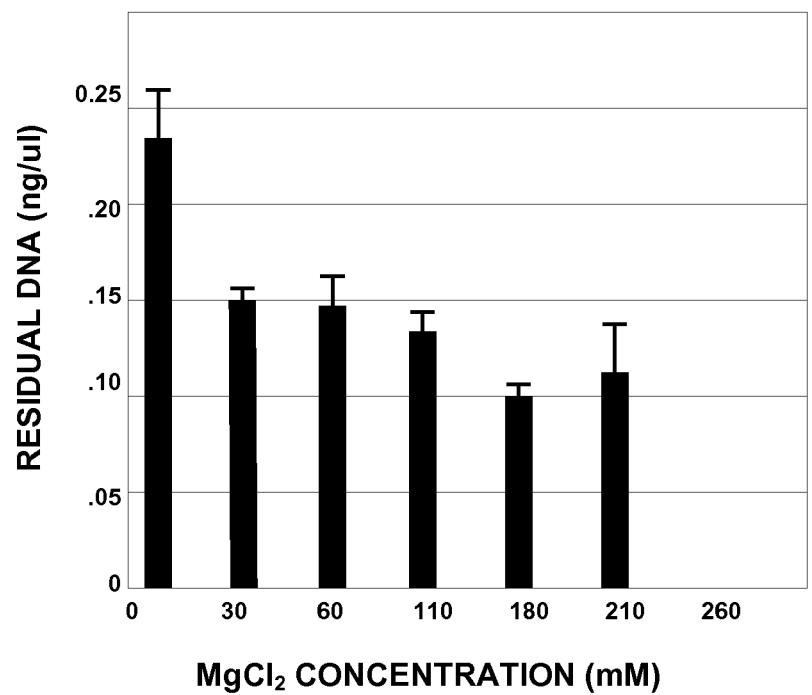

FIG. 3 is a bar graph showing the effect of $MgCl_2$ concentration (washing solution) on the amount of residual epithelial cell DNA present in a sample.

Figure 4A:
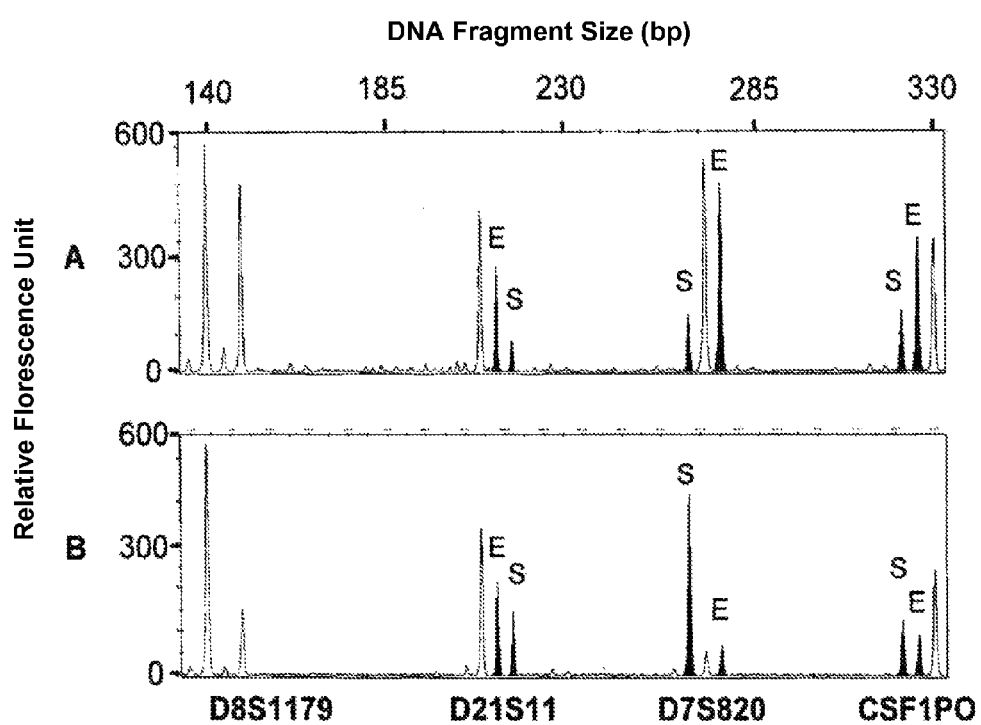
Figure 4B:
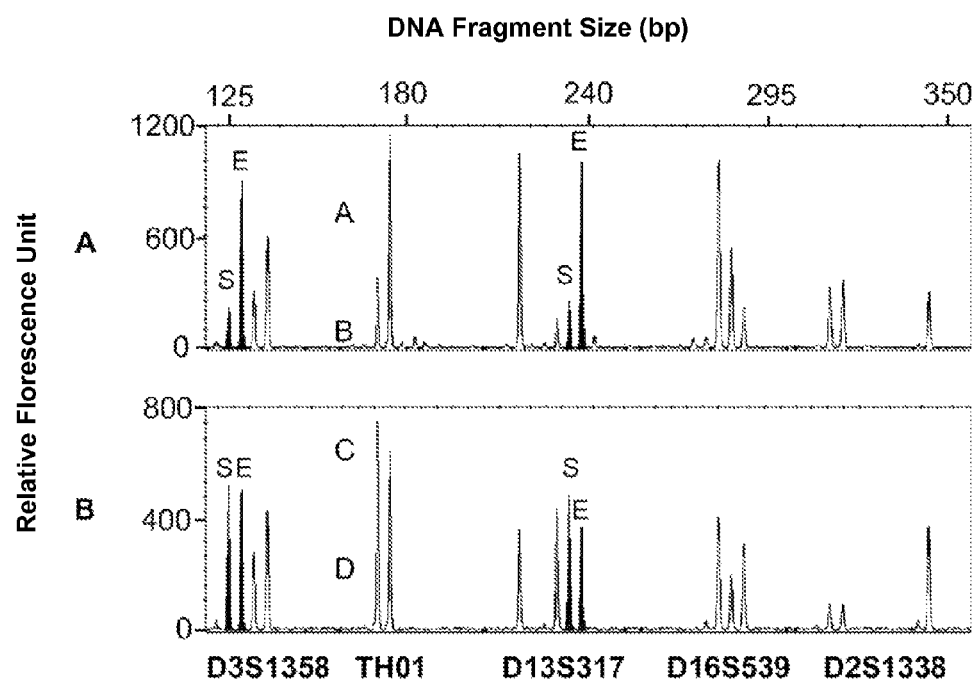
Figure 4C:
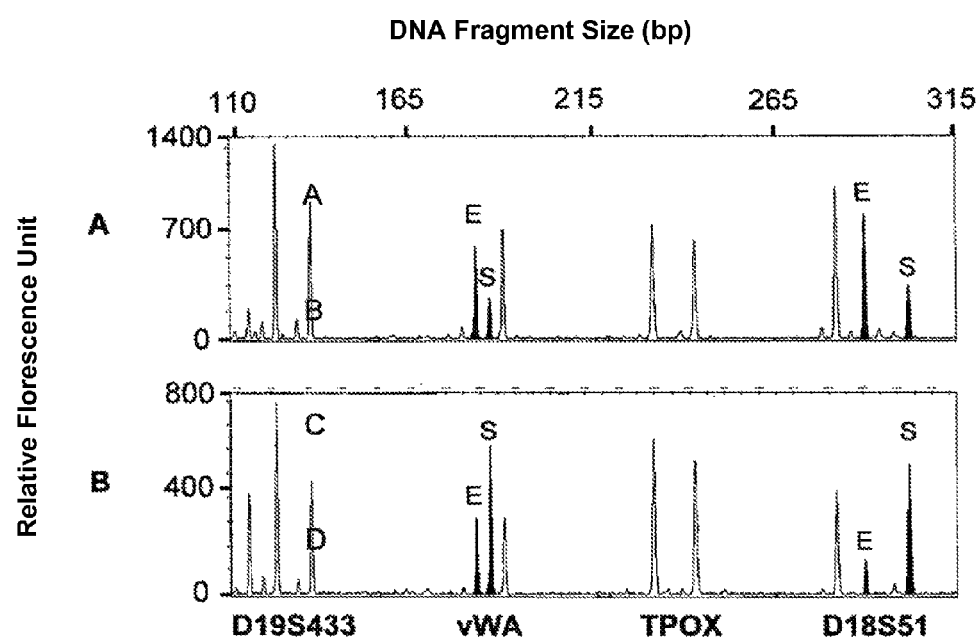
Figure 4D:
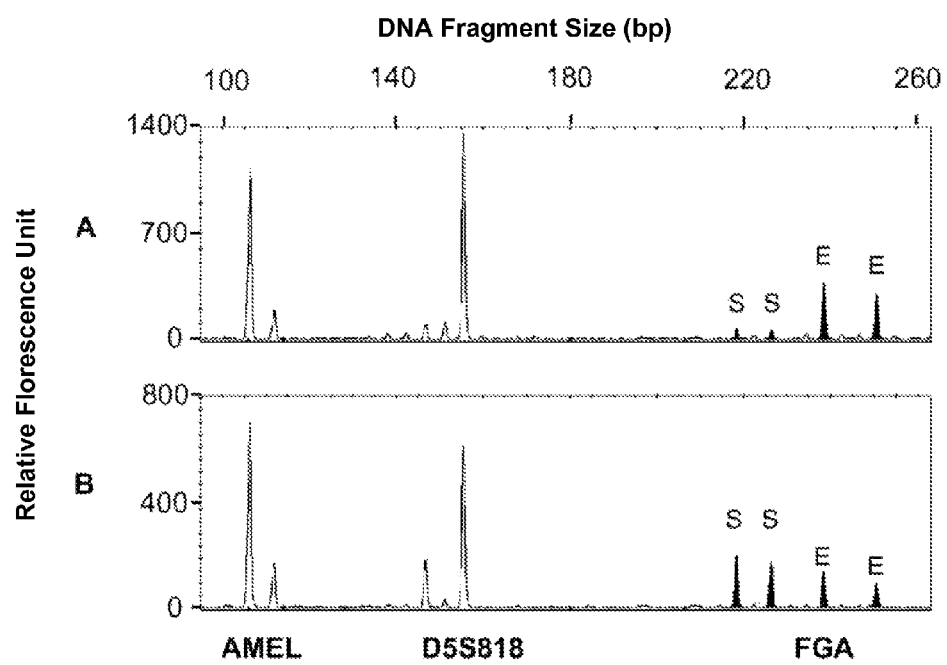

FIGS. 4A-4D are STR typing profiles of sperm DNA isolated with a method of the invention as illustrated in Example 3. Primers for the various loci were labeled with a fluorescent dye, followed by amplification of the various loci and separation of products by electrophoresis. Fluorescence excitation/emission wavelengths and dyes employed were 494/522 nm, 6-FAM (FIG. 4A), 538/554 nm, VIC (FIG. 4B), 546/575 nm, NED (FIG. 4C), 558/595 nm, PET (FIG. 4D).

DETAILED DESCRIPTION OF CERTAIN EMBODIMENTS OF THE INVENTION

Definitions

The term "nucleic acid," as used herein, encompasses DNA and RNA molecules, as well as DNA/RNA chimeras and nucleic acid molecules with unnatural bases and/or sugar moieties. In a particular forensic embodiment, DNA from sperm cells of the assailant is isolated from DNA of nonsperm cells (usually epithelial cells) of the victim.

The "sample" used in the present invention can be any heterogeneous cellular suspension containing two or more cell types wherein at least one of the types of cells can be selectively lysed. The sample also includes suspension medium such as reconstituting buffer which also contains impurities from the sample, e.g., extraneous DNA. In some embodiments, the sample is reconstituted from a forensic specimen, and can optionally include the swab or cotton applicator on which the forensic specimen is collected. It will be understood that after a washing solution is combined with the sample, the sample will also comprise a washing solution. Thus, separate recitation of the washing solution is not necessary.

The term "forensic specimen," as used herein, is a specimen obtained to address legal issues, including, but not limited to, murder, rape, trauma, assault, battery, theft, burglary, other criminal matters, identity testing, paternity testing, and mixed application samples. It broadly refers to a substrate which contains a specimen of biological materials such as blood, blood stains, saliva, skin debris, feces, feces stains, urine, sperm cells, epithelial cells, muscle tissue, bone or muscle remains, or mummified remains. In some embodiments, the "forensic specimen" is contained on, and includes, a swab or cotton applicator on which the biological specimen is collected.

The term "differential extraction," as used herein, refers to extraction methods used to separate nucleic acid from individual cell types within a heterogeneous population of cells, such as the selective lysis of sperm cells in an epithelial-sperm cell mixture.

The two or more "cell types" amenable for use in embodiments of the present invention can include any two or more of the following, as long as at least one cell type in the mixture can be selectively lysed: sperm cells, epithelial cells, erythrocytes, platelets, neutrophils, lymphocytes, monocytes, eosinophils, basophils, adipocytes, chrondrocytes, tumor cells, neurons, glial cells, astrocytes, red blood cells, leukocytes, macrophages, hair cells, bladder cells, kidney cells, retinal cells, rod cells, cone cells, antigen presenting cells, T-cells, B-cells, plasma cells, muscle cells, ovarian cells, prostate cells, vaginal epithelial cells, testicular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts and osteoclasts.

In certain embodiments, more than two cell types are present in the sample. In certain forensic embodiments, sperm cells and epithelial cells are essentially the only cell types present in the sample. In certain forensic embodiments, sperm cells, epithelial cells and leukocytes are the cell types present in the sample. In embodiments where leukocytes are present, the first wash step acts to lyse the leukocytes selectively, while keeping the sperm and epithelial cells intact.

"Sperm cell," as used herein, can include an intact sperm cell or essentially intact sperm cell, (e.g., a sperm cell that has lost its flagellum or tail) as long as the nucleus is still intact.

The term "cell mixture," as used herein, refers to a heterogeneous collection of at least two different cell types.

The "cell suspension medium" is a buffer, or liquid, in which the cell mixture is present. The cell suspension medium can be a reconstituting buffer, if the cell mixture was originally present on a solid substrate, or a washing solution, if isolated cells are resuspended in it. The reconstituting buffer can be, by way of nonlimiting example, 1× Phosphate-Buffered Saline (PBS). Cell suspension media are well-known and can be readily selected by those skilled in the art. For the purposes of this invention, a solution added to a cell suspension medium, e.g., washing solution, is part of the cell suspension medium, even if it is not originally present.

The term "supernatant," as used herein, describes the liquid, or buffer, present in the vessel, after cells and particles have settled to the bottom, or side, of the vessel. The supernatant can comprise impurities, such as DNA from compromised cells, or fibers from a swab, if the cell mixture was originally reconstituted from a solid substrate, or cell lysate after a lysis step has occurred, or spent washing solution after a wash step has occurred. Additionally, once the cells and particles have settled to the side or bottom of a vessel, the cell suspension medium can be considered a supernatant, and can comprise impurities. Thus, the usage and meaning of cell suspension medium and supernatant overlap.

"Residual DNA," as used herein, refers to extracellular DNA in the sample medium and not present within a cell, e.g., in a sperm-epithelial cell mixture, DNA from compromised or lysed cells. Residual DNA may be bound to or otherwise become associated with a cell's surface and potentially contaminate DNA extracted from the cell. In embodiments where leukocytes are present, residual leukocyte DNA is formed during the first wash step because the first wash step lyses the leukocytes.

A "vessel," for use with the present invention, can be any tube (e.g., 0.2 mL, 0.5 mL, 1 mL, 1.5 mL, 2 mL in volume), container, or well, which is open on the top, and enclosed on all sides and the bottom. Included in this definition are reagent cartridges, designed for automated equipment. Multiple wells can be joined together to form a plate, such as a 96-well plate or any other plate adapted to be used in automated equipment.

The term "particles responsive to a magnetic field," as used herein, is intended to encompass all particles (e.g., beads or irregular shape particles) that can capture, i.e., interact or associate with, cells or nucleic acid or both (under different buffer conditions) to accomplish sequestration of the cells from the medium, and which migrate when placed within a magnetic field. In some embodiments, more than one particle can associate with one another to form particle aggregates. In other embodiments, the particles are uniform in diameter and/or shape, e.g., beads. When a magnet or magnetic field is in close proximity to, or in contact with, the vessel, the particles in the reaction vessel migrate towards the source of the magnetic field. Included are ferromagnetic, paramagnetic, and superparamagnetic particles. Nonlimiting examples of commercially available particles responsive to a magnetic field are particles comprised of porous silica with supermagnetic core MP-50 (6.5 µm), MP-85 (>8 µm) (W.R. Grace, Columbia, Md.), iron oxide immobilized with streptavidin (Sigma, St. Louis, Mo.), and iron(III) oxide powder (5 µm) (Sigma, St. Louis, Mo.), DNA IQ™ silica particles (Promega, Madison, Wis.), MagPrep® silica particles (Novagen, San Diego, Calif.), BcMag® silica-modified magnetic beads (5 µm or 1 µm) (Bioclone Inc., San Diego, Calif.), supermagnetic silica particles (1 µm or 0.75 G. Kisker GbR, Steinfurt, Germany), and Dynabeads® (Invitrogen, Carlsbad, Calif.) with different type of surface functional groups (e.g., Dynabeads® MyOne carboxylic acid beads, Dynabeads® WCX, Dynabeads® TALON and Dynabeads® MyOne tosylactivated). The terms "particles," or "magnetic particles," as used herein, have the same meaning as "particles responsive to a magnetic field" and are simply shorthand for the longer term.

"Size exclusion filtration," as used herein, refers to a centrifugation process wherein a vessel containing a filter is subjected to centrifugation. The sample, lysis buffer, or washing solution is applied to the filter, optionally mixed with cells sequestered on the filter, and centrifuged. The filter allows components smaller than the size of the filter pore to be isolated (in the "filtrate") from components bigger than the size of the filter pore (i.e., cells). One example of a suitable spin filter is the Corning spinX Costar 8160 filter, with a pore size of 220 nm, available from Sigma (part # CLS8160). Other spin filters with similar pore sizes can also be employed. The pore size of the filter should not be larger than 2 µm, in order to keep epithelial cells from passing into the filtrate.

The term "short tandem repeat," or "STR," as used herein, refers to all sequences between 2 and 7 nucleotides long which are tandemly reiterated within a segment of the human genome.

DNA typing (or "genotyping") involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e., "locus") of DNA in which such a variation occurs is referred to as a "polymorphic locus."

Genetic markers which are sufficiently polymorphic with respect to length or sequence have long been sought for use in identity applications, such as paternity testing and identification of tissue samples collected for forensic analysis. The discovery and development of such markers and methods for analyzing such markers have gone through several phases of development over the last several years.

In recent years, the discovery and development of polymorphic short tandem repeats (STRs) as genetic markers has played an important role in DNA typing. In this approach, amplified alleles at each selected locus may be differentiated based on length variation. Amplification protocols with STR loci can be designed to produce small products, generally from 60 to 500 base pairs (bp) in length, and alleles from each locus are often contained within a range of less than 100 bp. This allows simultaneous electrophoretic analysis of several systems on the same gel or capillary electrophoresis by careful design of PCR primers such that all potential amplification products from an individual system do not overlap the range of alleles of other systems. These results can then be used for example to identify the parentage of human children, and to identify the source of blood, saliva, semen, and other tissue found at a crime scene or other sites requiring identification of human remains.

The term "selective sperm lysis buffer," as used herein, refers to a buffer that is capable of preferentially lysing sperm cells in a mixture comprising sperm cells and at least one other type of non-sperm cells (that are not susceptible to lysis by this buffer). "Preferentially lysing sperm cells" as used herein, refers to the lysis of sperm cells, whereas nonsperm cells are not lysed. Quantitatively, at least 80%, 85%, 90%, 95%, or 99% of the sperm cells are lysed, whereas at least 80%, 85%, 90%, 95% of the nonsperm cells are not lysed. In certain embodiments, only a negligible number of non-sperm cells are lysed together with the sperm cells. Nonlimiting examples of such buffers are a combination of 880 mM NaCl and 85 mM DTT, and are further described infra, specifically in Example 1. Selective sperm lysis buffers are disclosed in U.S. Prov. App. No. 60/899,106, incorporated herein by reference in its entirety. In some embodiments, selective sperm cell lysis buffers comprise at least one disulfide bond reducing reagent (e.g., dithiothreitol (DTT), tris(2-carboxyethyl)phosphine HCl (TCEP), mercaptoethanol (ME), glutathione (GSH)) and at least one salt reagent (e.g., sodium chloride (NaCl), potassium chloride (KCl), lithium chloride (LiCl), magnesium chloride ($MgCl_2$), magnesium sulfate ($MgSO_4$), sodium nitrate ($NaNO_3$), calcium chloride ($CaCl_2$), calcium sulfate ($CaSO_4$)). In certain embodiments, a selective sperm lysis buffer comprises at least one disulfide bond reducing reagent with a concentration of at least 0.01M, 0.05M, 0.1M, 0.2M, 0.3M, 0.4M, 0.5M, 0.7M or 0.8M. In certain embodiments, a selective sperm lysis buffer comprises at least one salt reagent with a concentration of at least 0.1M, 0.25M, 0.5M, 1M, 1.5M, 2M or higher.

The term "washing solution," as used herein, refers to a reagent with a function of removing residual DNA and other impurities contained in the supernatant from cells. In addition, the "washing solution" acts as a selective leukocyte lysis buffer, when leukocytes are present in a sample with sperm and epithelial cells. Washing solution can be, but is not limited to, water, 1×PBS, salt solutions such as $MgCl_2$, NaCl and KCl diluted in an appropriate buffer, e.g., water, 1×PBS, Tris-HCl, or other physiologically acceptable solution. In some embodiments, the washing solution is $MgCl_2$ diluted in 1×PBS.

In some embodiments, the washing solution is or comprises a DNase in its reaction buffer. In some embodiments, DNase is a component of the washing solution. In embodiments where DNase is a component of the washing solution, DNase can be added in conjunction with a cationic salt, such as $MgCl_2$. In yet other embodiments, a wash with a cationic salt can be immediately followed with a DNase wash (see, e.g., example 3 below). The two washes carried out in Example 3 correspond to the employment of steps 2 and 4 in FIG. 1.

In some embodiments, the forensic specimen is reconstituted directly in a washing solution.

DNase is salt sensitive and optimal DNase activity occurs in low salt solution (<20 mM). When wash solution containing high salt concentration, additional amount of DNase can be used to compensate for the reduced enzyme efficiency. A serial wash with a salt washing buffer followed by DNase should not hinder the enzyme's activity.

In some embodiments, the first or second or both washing solutions comprise DNase. In particular forensic embodiments, 0.01 U to 10 U of DNase is present in the washing solution. In embodiments where DNase is in the presence of a salt solution, up to 50 U of DNase can be employed.

In some embodiments, a washing solution can comprise a polyanion, such as heparin polyanion. Other examples of polyanions include poly(acrylic acid), poly(methacrylic acid), poly(styrene sulfonate), poly(2-acrylamido-2-methyl-1-propane-sulfonic acid) (PAMPS), or NAFION® (DuPont™). In some embodiments, the washing solution can comprise a polycation, such as poly-lysine, or a combination of polycations. Still, in some embodiments, the wash solution can comprise DNA from a non-primate source, such as salmon sperm DNA, to compete the female DNA from a sperm cell's surface. The washing solution can be combined with the sample medium or the medium can be removed and the washing solution freshly added. In some embodiments, forensic specimen is incubated in the wash solution for up to 24 hours before separating the mixed sperm and epithelial cells from the supernatant (which may contain leukocyte lysate).

When polyanion or polycation are included in the washing solution, the molar concentration of the polyanion or polycation should be in large excess to that of extraneous DNA molecules, in order to ensure that DNA bound to a cell's surface is replaced by polyanion or polycation. A typical forensic sample contains about 10 ng of extraneous DNA (Anal. Chem. 2005, V. 77, pp. 742-749). Assuming final volume of wash solution (with sample) is 500 μL, and DNA has been fragmented with a average length of 500 bp (the largest STR amplicon is about 500 bp), the molar concentration of DNA is about 60 pM. Based on estimated DNA concentration, one can select and optimize the optimal polyanion or polycation concentration for a particular washing solution. In addition, once the amount of extraneous DNA in the sample is known, one can also determine the amount of DNase needed for complete digestion of extraneous DNA for a given digestion time and temperature (e.g., room temperature, 37° C.). For example, one unit of Turbo DNase is defined as the amount of Turbo DNase required to completely degrade 1 μs of DNA in 10 min at 37° C. Therefore, one unit of Turbo DNase should be able to completely degrade all the extraneous DNA found in a typical sexual assault sample. However, excess amount of Turbo DNase (for example, 5 units or more) could be used to achieve shorter DNA digestion time and/or room temperature operation. When another type of DNase is used for the purpose of digesting extraneous DNA in a sexual assault sample, the optimal digestion condition (amount of DNase, digestion time and temperature) can be easily optimized experimentally.

"Nucleic acid capture particles" can be any particles that are responsive to a magnetic field which also bind to nucleic acid present in the sample or supernatant, under specific conditions (e.g., an appropriate buffer for nucleic acid capture). The "nucleic acid capture particles" can bind DNA or RNA preferentially, or all nucleic acid. For example, nucleic acid binds to silica magnetic particles in chaotropic buffer (U.S. Pat. No. 5,234,809, incorporated in its entirety by reference). Buffers that can be employed for nucleic acid capture, with nucleic acid capture particles, can be solutions prepared from guanidium isothiocyanate (GuSCN) and guanidium chloride. Nucleic acid can also be captured by magnetic particles in solution containing high salt and alcohol (see, e.g., U.S. Pat. Nos. 5,523,231 and 5,705,628, both incorporated herein, in their entirety, by reference). In some embodiments sodium acetate salt (2.5 M, pH 5.2) is used in conjunction with 70% ethanol. Other nucleic acid capture particles use buffers comprising 0.5 M to about 5.0 M salt combined with 7%-13% polyethylene glycol can be harnessed as a reaction buffer with capture particles. Salts such as sodium chloride, lithium chloride, barium chloride, potassium chloride, calcium chloride, magnesium chloride and cesium chloride can all be used.

The term "elution buffer," or "elution solution," as used herein, refers to a reagent with a function of disrupting or breaking the interaction of nucleic acid with nucleic acid capture particles. For example, the buffer can be any low salt solution (e.g., tris (10 mM)-EDTA (0.1 mM) (TE) buffer) or DNase-free water. Elution buffers are commonly employed, and are known in the art. Other low salt buffers (neutral to slightly basic pH) can also be used.

Specific Embodiments

By way of overview and introduction, the process of the present invention is given as FIG. 1. A sample comprising a mixed cell suspension, for example a forensic specimen, is provided at step 1. The sample can then washed with a washing solution at step 2. If leukocytes are present in the sample, they are lysed during the first wash step (either step 2 or 4), while keeping the sperm and epithelial cells intact. The cells in the sample are then isolated by a method chosen by the user at step 3, for example by size exclusion filtration (3.1), magnetic particles (3.2), centrifugation (3.3), or any other method known in the art. The isolated mixed cells can then washed with a washing solution at step 4. If the wash at step 2 is implemented, the wash at step 4 is not required. Similarly, if the wash is employed at step 4, the wash at step 2 is not required. However, both can be performed if desired (see Example 3). At step 5, sperm cells are selectively lysed, for example with the sperm lysis buffer disclosed in U.S. Provisional App. Ser. No. 60/899,106, the entire contents of which are incorporated by reference. Selective sperm lysis is followed by recovery of the sperm cell lysate, which contains sperm DNA, at step 6. Sperm DNA can then be optionally further isolated from the sperm cell lysate at step 7. These steps are discussed in turn.

A sample, if provided for example as a forensic specimen on a swab, is reconstituted prior to step 2, to form a cell suspension, for example, in a buffer comprising 1×PBS. In a particular forensic embodiment, a forensic specimen is reconstituted in the same vessel used for DNA isolation. In another forensic embodiment, a forensic specimen is reconstituted in a different vessel, and the cell suspension is transferred to the DNA isolation vessel. The vessel can contain magnetic particles or a size exclusion filter, or neither.

The swab itself can be removed, pushed aside, or it (or swab debris left after removal of the swab) can be digested using cellulose digesting enzymes. Examples of cellulose digesting enzymes include cellulase, beta-glucanase and those isolated from fungal sources such as *Aspergillus niger*, *Trichoderma reesei*, and *Trichoderma viride*. Although enzymes of this type can affect epitope stability on cell surface proteins, the cell membranes, and DNA content of the cells, will generally not be compromised. Nevertheless, such enzymes are also considered impurities and should be removed. The first washing step of the present process can help accomplish this.

In various embodiments, a forensic sample is reconstituted in about 1 mL reconstituting buffer (e.g., 1×PBS) and gently mixed in a vessel (which may or may not be the vessel used for cell sequestration and differential extraction). The substrate (e.g., a swab) is then removed from the vessel and the cells from the specimen centrifuged. The reconstituting buffer is then drawn off the cell pellet, and the cell pellet resuspended in 50 µL reconstituting buffer. In another embodiment, about 50 µL of the cell suspension medium is left on the cell pellet, with the rest of the medium drawn off, and the cell pellet reconstituted in the original medium (i.e., the 50 µL).

In some embodiments, including various forensic embodiments, a portion of the cell suspension can be used to count the number of cells originally present in the sample. The number of cells present can give the user of the method a basis for determining the quantity and/or concentration of particular reaction component to employ.

Once the cell sample is present in solution, it can be washed by combining the cell suspension with a washing solution (step 2). In preferred embodiments, the ratio of wash buffer to cell suspension is 10:1, 9:1, 8:1, 7:1, 6:1, 5:1, 4:1 or 3:1. Optionally, after the cell suspension is formed (either by initially providing mixed cells in solution, or by reconstituting a sample), it can be centrifuged and resuspended in resuspension buffer (e.g., 1×PBS), to form a more concentrated suspension. In preferred embodiments, the cell suspension used throughout the process of the invention has a volume ranging from 50 µL to 2 mL.

At step 2, the sample can be washed by combining a wash solution with the cell suspension, followed by mixing the two components. Mixing can be accomplished by pipetting, vortexing or shaking the vessel, e.g., with an orbital shaker or by manual rotation. The two components can also be mixed by passive diffusion. The cell suspension wash can be carried out in a vessel separate from the one used for sperm cell lysis and DNA isolation, or in the same vessel. Washing solutions are described supra. Samples in the wash solution can be incubated for up to 24 hours, if desired.

In some embodiments, a forensic specimen on a swab, applicator, or portion thereof, is reconstituted directly in a wash solution. In certain forensic embodiments, the swab itself is removed after incubation in the wash solution. In certain forensic embodiments, the swab is not removed after incubation in the wash solution. In a particular forensic embodiment, a forensic specimen is reconstituted in the same vessel used for DNA isolation. In another forensic embodiment, a forensic specimen is reconstituted in a different vessel, and the cell suspension is transferred to the DNA isolation vessel. The DNA isolation vessel can contain magnetic particles or a size exclusion filter, or neither.

In some embodiments, including various forensic embodiments, a portion of the cell suspension can be used to count the number of cells originally present in the sample. The number of cells present can give the user of the method a basis for determining the quantity and/or concentration of particular reaction component to employ.

Various cell isolation procedures can be employed at step 3, depending on the preference of the user of the method. For example, the cells in the cell suspension can be isolated by particles responsive to a magnetic field (3.2), as fully described in U.S. Provisional App. Ser. No. 60/890,460, a copy of which is attached as Appendix A and which is incorporated by reference herein in its entirety. Briefly, while the vessel, containing the cell suspension is in the presence of a magnetic field, the particles push the cells towards the source of the magnetic field and the cell suspension medium along with the impurities is removed, whereas the particles and cells remain in the vessel. The removal of the cell suspension medium can be accomplished in an automated fashion or manually, by pipetting or aspirating, both gentle techniques that avoid damage to the cells.

Although ionic interaction and/or hydrophobic interaction contribute to the cell/particle(s) association, cell and particle association can also be established by physical trapping or temporary attachment of particles to the cell under magnetic force if particles are smaller than cells, or physical trapping or temporary attachment of cell to particle or particle aggregates under magnetic force if cells are smaller than the particle or particle aggregates. Other particle embodiments can employ particles that sequester cells based on other non-covalent interactions. Some non-covalent interactions that can be employed are hydrogen bonding, cation-π, π-π interactions, dipole-dipole, dipole-induced-dipole, charge-dipole and van Der Waals interactions.

The particles that will sequester sperm and epithelial cells will typically have a diameter within the range of 0.5-100 µm; preferably 1-10 µm with sizes outside the broader range not being excluded. The exact limits of the size range can be ascertained for a given situation of particles and cells by routine experimentation.

In various embodiments, the cells are initially sequestered at step 3.3 from the impurity containing cell suspension medium by centrifugation (to form a cell pellet). The cell suspension medium (i.e., the supernatant) is then removed either in an automated fashion, or manually (e.g., by pipetting), to isolate the cells from the sample (containing residual DNA from damaged epithelial cells). Instruments amenable for use with the present invention include, but are not limited the Beckman Biomek® (Beckman Coulter, Fullerton, Calif.) or a Tecan liquid automated handling system (e.g., Freedom Evo® Services Tecan Systems, San Jose, Calif.).

In other embodiments, size exclusion filtration is employed to isolate sperm and epithelial cells from a sample (step 3.1). In various size exclusion filtration embodiments, the cell suspension can be initially washed with washing solution, and the wash can be accomplished directly on the filter, or in another vessel. The washing solution/cell suspension mixture, once applied to the size exclusion filter, is centrifuged. The filtrate, containing impurities that were bound to the cells, is then removed. The cells originally present in the sample are isolated on the filter. In various specific embodiments, the spin filter used is a Corning spinX Costar 8160 filter, with a pore size of 220 nm, available from Sigma (part # CLS8160). Other spin filters with similar pore sizes can also be employed. The pore size of the filter should not be larger than 2 µm, in order to keep epithelial cells from passing into the filtrate.

In some embodiments, size exclusion filtration is employed to isolate sperm and epithelial cells from a sample with swab in the wash solution (step 3.1). The washing solution/cell suspension mixture and swab, once applied to the size exclusion filter, is centrifuged. The filtrate, containing impurities such as extraneous DNA, is then removed. The cells originally present in the sample are isolated on the filter. The swab containing trapped cells is also retained on the filter. In various specific embodiments, the spin filter used is a Corning spinX Costar 8160 filter, with a pore size of 220 nm, available from Sigma (part # CLS8160). Other spin filters with similar pore sizes can also be employed. The pore size of the filter should not be larger than 2 µm, in order to keep epithelial cells from passing into the filtrate.

Although centrifugation, size exclusion filtration (using centrifugation) and particle trapping are described here for isolating cells, the present invention is not limited to these techniques. For example, cells can be isolated by the methods described in U.S. Published Application No. 2005/0032097 ("the '097 Publication"), incorporated by reference in its entirety. The '097 Publication describes a process for the isolation of sperm DNA from a sample containing both sperm and non-sperm cells. Briefly, selective lysis of non-sperm cells is carried out initially, with SDS and proteinase K. Sperm cells are then isolated from the non-sperm cell lysate by vacuum filtration using a 2 µm pore size. The filtrate is then removed and sperm cells are digested on the filter using a reducing agent such as β-mercaptoethanol, dithiothreitol, reduced glutathione, or combinations thereof. The sperm DNA is then isolated from the solubilized sperm.

In other processes, antibody coated particles can be used to bind cell surface proteins distinct to one type of cell. In addition, flow cytometry and vacuum filtration can be used to selectively isolate cells.

Once cells are isolated from the remainder of the cell suspension medium, another wash of the cells can be employed. In various embodiments, the washing solution is salt solution such as $MgCl_2$ diluted in 1×PBS. In these embodiments, the final concentration of $MgCl_2$ can range from about 20 mM to 300 mM. This $MgCl_2$ concentration range can also be used for the initial wash step 2. In various embodiments, TURBO™ DNase, available from Applied Biosystems and Ambion® (Foster City, Calif., part # AM2238), or DNase I supplied by Ambion® (Catalog# AM222) is employed as in washing solution to digest the extraneous DNA. Alternatively, other commercially available DNase enzymes can be used.

In some wash solution embodiments, DNase is used in conjunction with $MgCl_2$, in the same solution. In other embodiments, a wash with a cationic salt (e.g., $MgCl_2$) (step 2 or 4 in FIG. 1) is immediately followed by a wash with a DNase enzyme (e.g., by carrying out both steps 2 and 4 in FIG. 1, or if step 2 is omitted, by repeating steps 3 and 4 twice). In yet other embodiments, a DNase wash (e.g., step 2 or 4 in FIG. 1) is followed by a wash with a cationic salt.

In some embodiments, the washing solution comprises heparin or other polyanions such as poly(acrylic acid), poly(methacrylic acid), poly(styrene sulfonate), poly(2-acrylamido-2-methyl-1-propane-sulfonic acid) (PAMPS), or NAFION® (DuPont™), diluted in a physiologically acceptable buffer. In some embodiments, the washing solution comprises a polycation such as poly-lysine. Still, in some embodiments, the wash solution can comprise DNA from a non-primate source, to compete the female epithelial DNA from a sperm cell's surface. In various embodiments, the wash is carried out in one or multiple serial steps with the same or different washing solutions.

In certain embodiments using centrifugation, cells are pelleted prior to a wash step and the cell pellet is washed by resuspending it in washing solution, (see FIG. 1, step 4) to selectively lyse leukocytes if present and disrupt any cell-impurity, or specifically cell-nucleic acid interactions that may exist. The washing solution, in some embodiments, comprises $MgCl_2$, KCl or NaCl. The salt concentration is high enough to achieve the desired function of breaking leukocytes and to disengage DNA from the sperm and epithelial cells' surfaces. Once the wash is completed, the cells are recentrifuged to form a washed cell pellet and the supernatant containing spent washing solution is removed. Removal of the supernatant can be done manually or in an automated fashion. Cell washing, recentrifugation, and wash buffer removal can be repeated, if desired. If these steps are repeated, the wash buffer can be the same or different. In the present methods, centrifugation is typically carried out at 18 k RCF for 1 min., although other conditions are within the scope of the invention.

In certain embodiments using size exclusion filtration, a washing solution is applied to the filter where the cells are captured. The washing solution is pipetted up and down onto the filter to dislodge the capture cells and to insure all sides of the cells are washed. Once the cells are mixed with washing solution, a centrifugation step is employed to recapture the cells (now washed) on the size exclusion filter. The filtrate, containing spent washing solution, is discarded. These steps encompass step 4 in FIG. 1.

In certain embodiments using magnetic particles, a wash is carried out by mixing a washing solution with the isolated cells and magnetic particles. For mixing to be complete, the magnetic field should be removed from the vicinity of the vessel wherein the reaction is taking place. Once mixing is accomplished, the magnetic field can be reapplied to the vessel to sequester the cells and particles from the spent washing solution. The spent washing solution is then removed.

In some embodiments, and regardless of the method used for cell isolation, a wash with multiple components is employed (step 2 or 4, FIG. 1). For example, a first component can be an $MgCl_2$ wash or polyanion wash or polycation wash, or a combination thereof and a second component can be a DNA degradation step with a DNase enzyme. These components can be mixed and then added to the sample.

Any DNase that does not lyse sperm cells partially or in their entirety, can be employed. DNase, present in a DNase reaction buffer (e.g., Turbo™ DNase from Applied Biosystems and and Ambion®), can be added and mixed with the sequestered cells as described above for other wash embodiments. DNase in its buffer is added to the sequestered cells, and mixed. In the particle embodiments, the magnetic field is removed from the vessel upon mixing. The magnetic field is then reapplied, or a centrifugation step employed, depending on the particular embodiment, to sequester the cells from the now contaminated (i.e., spent) washing solution. Any remaining DNase, along with the DNase reaction buffer (with degraded DNA present), is then removed in an automated fashion or manually, by pipetting or aspirating. One or more additional washing solutions are then added to the sequestered cells in a serial manner, if desired.

In other embodiments, a wash step is performed prior to and after DNase treatment of the sample. In these embodiments, the first wash step can be accomplished before and/or after initial cell sequestration (i.e., at step 2 or 4). In these embodiments, a minimum of three serial washes are carried out.

Once the cells are washed and isolated (regardless of method) from the spent washing solution (i.e., cell suspension medium), the sperm cells are lysed (FIG. 1, step 5).

Selective sperm lysis buffers that can be used in certain embodiments are disclosed in co-pending commonly owned U.S. Prov. App. Ser. No. 60/899,106, incorporated by reference in its entirety.

In some embodiments, selective sperm cell lysis buffers comprise at least one disulfide bond reducing reagent (e.g., dithiothreitol (DTT), tris(2-carboxyethyl)phosphine HCl (TCEP), mercaptoethanol (ME), glutathione (GSH)) and at least one salt reagent (e.g., sodium chloride (NaCl), potassium chloride (KCl), lithium chloride (LiCl), magnesium chloride ($MgCl_2$), magnesium sulfate ($MgSO_4$), sodium nitrate ($NaNO_3$), calcium chloride ($CaCl_2$), calcium sulfate ($CaSO_4$)). Other sperm selective lysis buffers, e.g., 10% β-mercaptoethanol combined with 2 M DTT, can be employed.

The concentration of the salt reagent in the selective sperm lysis buffer can be at least 0.1 M. 0.5 M, 1 M, 2 M or higher. The concentration of the disulfide bond reducing reagent can be at least 0.01 M, 0.05 M, 0.1 M, 0.2 M, 0.3 M, 0.4 M, 0.5 M, 0.7 M or 0.8 M.

In particular embodiments selective sperm lysis buffers for use with the present invention include, but are not limited to: (1) 880 mM NaCl and 85 mM DTT prepared in 1×PBS, (2) 700 mM KCl and 85 mM DTT prepared in 1×PBS and 260 mM $Mg_2Cl$ and (3) 85 mM DTT prepared in 1×PBS.

Based on the components taught for the selective sperm lysis buffer, one of skill in the art can optimize the final concentration of the salt and disulfide bond reducing reagent to lyse the sperm cells while keeping the non-sperm cells essentially intact. One nonlimiting example of selective sperm lysis buffer is buffer comprising 200 mM DTT and 1 M KCl. Other combinations of a disulfide bond reducing reagent and salt, as described supra may be used at these respective concentrations. In some embodiments, more than one salt can be employed with one disulfide bond reducing agent. In various embodiments, more than one disulfide bond reducing agent is employed with one salt.

In various embodiments of the invention, mixing the selective sperm lysis buffer with the sequestered cells can be accomplished by pipetting up and down into the vessel. In some embodiments, the selective lysis buffer and cell population are combined and vortexed at a low speed, in order to allow for full interaction between cells and lysis buffer. In some embodiments, the cells are lysed by diffusion. Lysis buffer conditions and type of mixing employed influence the duration of the lysis step. These conditions can be optimized using no more than ordinary skill and optimization is dependent on the particular application (e.g., forensic or not, types of cells involved etc.) of the present methods. In some embodiments, this step, and the other steps of the present invention, are carried out in an automated fashion.

In various particle embodiments, selective sperm lysis buffer is added before discontinuation of the magnetic field. In some embodiments, selective lysis buffer is added after discontinuation of the magnetic field.

In certain embodiments, the components of the selective sperm lysis buffer are added sequentially with the isolated cells and mixed one-by-one with the cells. Alternatively, mixing does not occur until both components (i.e., the salt and disulfide bond reducing agent) are added. In some embodiments, the disulfide bond reducing agent is added first. In some embodiments, lysis occurs by passive diffusion and, therefore, mixing is not performed by the user. In various embodiments, mixing occurs by a combination of passive mixing and active mixing (e.g., by vortexing or pipetting).

In various embodiments, incubation with selective sperm lysis buffer is carried out at any temperature for a length of time sufficient to achieve the appropriate results. In certain embodiments, the incubation is carried out at room temperature. Alternatively, the incubation can be carried out at approximately 20-50° C. The incubation interval ranges from about 1 minute to 4 hours or longer, with more specific typical intervals being 5 minutes or 10 minutes.

In particle embodiments, the sperm cell lysate can be recovered at step 6 from the reaction vessel by reapplying a magnetic field to the reaction vessel, thereby sequestering the cells that were not lysed (and the particles). The supernatant, after selective lysis, will include the sperm cell lysate, and can be subsequently removed from the vessel. This can be accomplished in an automated fashion, or manually by pipetting. An optional wash can be performed at this stage to further reduce any nucleic acid from the first lysate that would contaminate the intact cells of the epithelial cells, if epithelial cell analysis is desired.

In centrifugation embodiments, selective sperm lysis buffer is added to the washed cell pellet at step 6, and mixed. Similarly, in size exclusion filtration embodiments, selective sperm lysis buffer is added to the filter and pipetted up and down (either manually or in an automated fashion), to dislodge the cells from the filter, and to ensure all cells interact with the lysis buffer. Once lysis is complete, a centrifugation step is carried out and the supernatant, containing sperm lysate, including sperm nucleic acid (in embodiments using centrifugation) or the filtrate, containing sperm lysate, including sperm nucleic acid (in embodiments using size exclusion) is recovered. Centrifugation, used alone or as part of a size exclusion technique, can be carried out, e.g., for 1 min. at 9K RCF (i.e., 10,000 RPM in a Beckman Coulter Microfuge 18 centrifuge). For the purposes of this invention, any centrifuge amenable to the vessels defined herein can be employed for the various method steps.

In some embodiments, the DNA, mRNA, or total RNA is purified from the sperm lysate at step 7, in preparation for a downstream application, such as amplification, sequencing or STR analysis, all of which are known analytical methods. Purification can be employed in any vessel, or predispensed reagent cartridge. Purification methods are well known in the art, see, e.g., U.S. Pat. Nos. 5,234,809, and 5,705,628, incorporated in their entirety herein. Extraction with guanidinium thiocyanate-phenol-chloroform, ethanol, and solid phase binding methods are all within the scope of the invention. Some solid phases that can be harnessed as substrates for DNA isolation are magnetic, styrene, and/or silica particles. In addition, nitrocellulose can be used to isolate DNA. Purification can entail mixing the lysate with nucleic acid capture particles and an appropriate buffer for nucleic acid, or in a various embodiments, DNA capture.

In various particle embodiments, the particles for cell trapping could also be used for DNA purification (step 7) under appropriate conditions. For example, when magnetic silica particles are used to trap cells, the trapped cells can be lysed and the released DNA can be captured and purified by the same trapping particles based on standard silica/chaotropic chemistry (e.g., U.S. Pat. No. 5,234,809 incorporated by reference in its entirety). In another example, if Dynabeads® MyOne carboxylic acid beads or magnetic iron oxide particles are used for cell trapping, DNA precipitation chemistry can be used to purify DNA after cell lysis (see, e.g., U.S. Pat. No. 5,523,231, U.S. Pat. No. 5,705,628 both incorporated in their entirety by reference).

In an embodiment where the sperm nucleic acid is purified with magnetic particles, an elution buffer is used to concentrate the nucleic acid in solution, and out of the solid state. Nonlimiting examples of elution buffers include deionized water, TE buffer, and any other low-salt buffer. In addition, heat may be added to the elution reaction during this step.

In some embodiments, the sperm lysate can be used for downstream reactions (e.g., nucleic acid amplification or sequencing), without further purification.

In certain embodiments, the methods of the present invention further comprise isolation and recovery of an epithelial cell's nucleic acid, after removal of the sperm cell's lysate. In some embodiments, the original sample contains sperm and epithelial cells and lysis of the epithelial cells need not be selective. Non-selective lysis may be carried out, for example, with a chaotropic, high salt, or detergent-based lysis buffer using methods well known in the art. In various embodiments, lysis can be carried out by subjecting the cells to heat, in order to break open the cells. Isolation and analysis of the epithelial cells in addition to the sperm cells permits assailant and victim to be both identified and associated.

In various embodiments of the invention, and in order to lyse a second specific cell type, the selective lysis buffer, or a general lysis buffer (depending on the contents of the original sample and the specific purpose of nucleic acid recovery) is mixed with the sequestered cells by pipetting up and down into the vessel. The epithelial cells are sequestered and isolated at step 6, when the sperm cell lysate is recovered.

In some embodiments, the second lysis buffer and cell population are vortexed, in order to allow for full interaction between cells and lysis buffer. In some embodiments, the cells are lysed passively by diffusion without vortexing or active mixing. Lysis buffer conditions and type of mixing employed dictate how long the lysis step is carried out for. These conditions can be optimized and are dependent on the particular application.

In other embodiments, the epithelial cells are present on a size exclusion filter in a vessel, and a lysis buffer is introduced to the top of the filter. The lysis buffer can then be pipetted up and down to dislodge the cells from the filter and to break up the cells, or allowed to incubate on the filter for a period of minutes. The vessel is then centrifuged and the epithelial cell lysate is present in the filtrate.

In some embodiments, the epithelial lysate is purified in another vessel, or specifically a compartment of a predispensed reagent cartridge, with magnetic particles and an appropriate buffer (suitable for binding of nucleic acid to particles). This step is accomplished in a similar fashion to the embodiment describing the isolation of the nucleic acid of the first cell type.

In embodiments using particles, the nucleic acid (either DNA or RNA, preferably DNA) can be isolated further from the epithelial or sperm lysate using the same particles originally used to sequester the cell populations. DNA is purified by the particles in the original vessel by changing the buffer conditions depending on the types of magnetic particles used for sequestering (e.g., by adding heat, salt, increasing or decreasing pH, etc.) in the vessel. For example, if the sequestering particles are magnetic silica particles, DNA can be captured by the particles in the original vessel by adding 5M GuSCN (guanidine thiocyanate) solution to the vessel. DNA on the particles is then washed with ethanol. Elution of the nucleic acid can then be carried out as described above. Alternatively, DNA isolation from the cell lysate can be carried out by other commercially viable protocols, such as those supplied by Promega (Madison, Wis.) under the trade names DNA IQ™.

In some embodiments, the second cell lysate is also removed from the vessel, either in an automated fashion, or manually, as described supra. The lysate can then be introduced into downstream assays that are well known in the art, for example, nucleic acid purification, amplification, sequencing or STR typing.

In various embodiments, the components to carry out selective sperm lysis, and recovery of its nucleic acid, in a sample containing more than one cell type, are supplied as a kit. In particle embodiments, a specific kit includes at least one reaction vessel, a quantity of particles responsive to a magnetic field, predetermined to be sufficient to sequester cells in a sample containing a specific quantity of cells, a quantity of washing solution sufficient to wash at least cells of one cell type, a quantity of selective lysis buffer sufficient to lyse the cells of the first type, a quantity of a general or selective lysis buffer, sufficient to lyse cells of the second cell type, and instructions for use. In some embodiments, the washing solution is $MgCl_2$ diluted in 1×PBS with a final $MgCl_2$ concentration of 260 mM. In other embodiments, the washing solution is comprised of components used in a serial manner, e.g., DNase supplied in a reaction buffer, and/or 1×PBS, 1× $MgCl_2$ or polyanion or polycation. The present method can be practiced with existing instrumentation which provides a source of a magnetic field. Sequestration of cells can be discerned visually.

In some non-particle embodiments, a specific kit includes at least one reaction vessel, optionally a size exclusion filter that fits in the reaction vessel, a quantity of washing solution sufficient to wash at least cells of one cell type, a quantity of selective lysis buffer sufficient to lyse the sperm cells, a quantity of a general or selective lysis buffer, sufficient to lyse epithelial cells, and instructions for use. In some embodiments, the washing solution is $MgCl_2$ diluted in 1×PBS. In other embodiments, the washing solution is comprised of components used in a serial manner, and can be selected from DNase supplied in a reaction buffer, 1×PBS, 1× $MgCl_2$, polyanions and polycations. However, the present invention is not limited to these wash components.

The present invention is further illustrated by reference to the Examples below. However, it should be noted that the Examples, like the embodiments described above, are illustrative and are not to be construed as restricting the enabled scope of the invention in any way.

Example 1—Comparing Differential Extraction Procedures: The Prior Art Washing Solution (1×PBS) Vs. $MgCl_2$ Washing Solution 500 µL $MgCl_2$ washing solution (260 mM final concentration, in 1×PBS) or 1×PBS was added to cell suspension samples containing 50 µL of a heterogeneous cell suspension, containing approximately 10,000 epithelial cells, 1,000 sperm cells and impurities, including residual DNA. The samples with the washing solutions were then transferred to spin filter tubes (Corning spinX Costar 8160, pore size of 220 nm). The tubes were centrifuged at 14,000 RPM in a Beckman Coulter Microfuge 18 centrifuge, after which, the filtrate was discarded.

200 µL selective sperm lysis buffer, comprising 875 mM $NaCl_2$ and 85 mM dTT, diluted in 1×PBS was added to the spin filter tubes. Sperm cells were then lysed by mixing, for approximately 5 minutes. The tubes were centrifuged at 14,000 RPM in a Beckman Coulter Microfuge 18 centrifuge to separate the sperm lysates from intact epithelial cells.

Next, sperm DNA purification was carried out using Applied Biosystems' proprietary DNA purification method. DNA can also be purified using commercially available kits such as DNA IQ™ from Promega. After DNA purification, the sperm DNA was quantified using the Quantifiler® Y Human Male DNA Quantification Kit (Applied Biosystems, Foster City, Calif.) and the epithelial DNA is quantified using the Quantifiler® Human DNA Quantification Kit (Applied Biosystems, Foster City, Calif.).

Approximately 1 ng of sperm or epithelial DNA was used for each amplification reaction. STR amplification was carried out using AmpFlSTR® Indenfiler® PCR Amplification Kit (Applied Biosystems, Foster City, Calif.) on a GeneAmp® PCT System 9700 (Applied Biosystems, Foster City, Calif.) according to the manufacturer's protocol.

STR typing was carried out using ABI PRISM 3100 Genetic Analyzer and data was analyzed using GenMapID3.2.

Results of sperm cell analyses are given in FIGS. 2A-2D, along with STR typing of control samples of sperm DNA and epithelial DNA. The respective loci names are listed below the corresponding peaks. Peaks are labeled E or S for specific epithelial cell and sperm cell peaks, respectively. As can be seen in these Figures, a $MgCl_2$ wash serves to eliminate contamination of epithelial cell DNA, more so than a 1×PBS wash. The STR peaks for the epithelial fraction are higher for the 1×PBS wash than for the $MgCl_2$ wash.

Example 2—$MgCl_2$ Washing Solution Reduces Extraneous Epithelial DNA from an Epithelial Cell Sample It has been found that $MgCl_2$ in a range of concentrations from zero to 260 mM is effective in removing surface bonded DNA more so than when a classical washing solution, 1×PBS, is used (FIG. 3). The epithelial cell samples were first washed with $MgCl_2$, diluted in 1×PBS and then mixed. Wash buffer was removed and the cells were incubated with a selective sperm lysis buffer. Lysis was implemented for 5 minutes, after which the sample was filtered and the DNA in the filtrate was purified and quantified. Because the lysis buffer is selective, what is left in the filtrate is residual epithelial DNA originally present in the sample. As can be seen in FIG. 3, the amount of residual DNA is reduced with an $MgCl_2$ concentration as low as 30 mM, as compared to the 1×PBS control. The optimal $MgCl_2$ concentration, as evident from FIG. 3, is between 160 mM and 260 mM.

Example 3—Comparing Differential Extraction Procedures: No DNase Wash Vs. DNase Wash Five hundred μL $MgCl_2$ washing solution (260 mM final concentration, in 1×PBS) was added to cell suspension samples containing 50 μL of post-coital samples. After mixing and incubation at room temperature for 5 minutes, the samples with the washing solutions were transferred to spin filter tubes (Corning spinX Costar 8160, pore size of 220 nm). The tubes were centrifuged at 14,000 RPM in a Beckman Coulter Microfuge 18 centrifuge, after which, the filtrate was discarded.

One hundred μL DNase wash solution, containing 10 units of Turbo DNase (AM2238, Applied Biosystems, Foster City, Calif.), was added to one of the two samples in the spin filter tubes. DNase wash was carried out at 37° C. for 5 minutes. The tubes were centrifuged at 14,000 RPM in a Beckman Coulter Microfuge 18 centrifuge, after which, the filtrate was discarded. The application of the two wash solutions ($MgCl_2$ and DNase) corresponds to step 2 in FIG. 1.

Next, 200 μL selective sperm lysis buffer, comprising 875 mM $NaCl_2$ and 85 mM dTT, diluted in 1×PBS was added to the spin filter tubes. Sperm cells were then lysed by mixing, for approximately 5 minutes. The tubes were centrifuged at 14,000 RPM in a Beckman Coulter Microfuge 18 centrifuge to separate the sperm lysates from intact epithelial cells.

Next, sperm DNA purification was carried out using Applied Biosystems' proprietary DNA purification method. DNA can also be purified using commercially available kits such as DNA IQ™ from Promega. After DNA purification, the sperm DNA was quantified using the Quantifier® Y Human Male DNA Quantification Kit (Applied Biosystems, Foster City, Calif.) and the epithelial DNA is quantified using the Quantifiler® Human DNA Quantification Kit (Applied Biosystems, Foster City, Calif.).

Approximately 1 ng of sperm or epithelial DNA was used for each amplification reaction. STR amplification was carried out using AmpFlSTR® Indenfiler® PCR Amplification Kit (Applied Biosystems, Foster City, Calif.) on a GeneAmp® PCT System 9700 (Applied Biosystems, Foster City, Calif.) according to the manufacturer's protocol.

STR typing was carried out using ABI PRISM 3100 Genetic Analyzer and data was analyzed using GenMapID3.2.

Results of sperm cell analyses are given in FIGS. 4A-4D. The respective loci names are listed below the corresponding peaks. Peaks are labeled E or S for specific epithelial cell and sperm cell peaks, respectively. As can be seen in these Figures, a DNase wash after a $MgCl_2$ wash serves to eliminate contamination of epithelial cell DNA, more so than an $MgCl_2$ wash without a DNase wash. The STR peaks for the epithelial fraction are higher for no DNase wash than for the DNase wash.

I claim:

1. A method for selectively recovering DNA from sperm cells in a sample containing mixed sperm cells and epithelial cells and a cell suspension medium comprising impurities, said impurities including contaminating residual DNA, the method comprising the steps of:
    (i) isolating the mixed sperm and epithelial cells from the cell suspension medium in a first isolating step;
    (ii) lysing selectively the sperm cells from the mixed sperm and epithelial cells;
    (iii) recovering the DNA from the lysed sperm cells; and
    (iv) at least two washing steps comprising:
        (a) washing the sample by mixing it with a first washing solution comprising from 20 mM to 300 mM $MgCl_2$ thereby disengaging residual DNA from the surface of the mixed sperm and epithelial cells prior to said first isolating step; and
        (b) washing the first isolated mixed sperm and epithelial cells with a second washing solution comprising DNase followed by isolating the washed mixed cells from the second washing solution in a second isolating step, prior to said lysing step.

2. The method of claim 1, wherein the DNase is 0.01 U to 50 U per 100 μl.

3. The method of claim 1, wherein the mixed sperm and epithelial cells are isolated by magnetic particles, size exclusion filtration, or centrifugation, in said first or second isolating step, or in both isolating steps.

4. The method of claim 3, wherein the mixed sperm and epithelial cells are isolated by magnetic particles in said first isolating step and centrifugation in said second isolating step.

5. The method of claim 3, wherein at least one of the first isolating step and second isolating step comprises:
combining magnetic particles with the sample in a vessel;
applying a magnetic field to the vessel, causing the particles to move in the direction of said field, thereby sequestering the cells from the sample; and
isolating the cells from the cell suspension medium.

6. The method of claim 5, wherein the lysing step comprises:
discontinuing the magnetic field applied to the vessel; and
mixing selective sperm lysis buffer with the cells and magnetic particles, thereby forming a lysate containing sperm DNA.

7. The method of claim 6, wherein the recovering step comprises:
applying a magnetic field to the vessel, thereby sequestering the particles and remaining cells from the lysate; and
recovering the lysate containing sperm DNA.

8. The method of claim 5, wherein the second washing step (b) comprises:
discontinuing the magnetic field applied to the sample;
combining a second washing solution with the mixed cells;
re-applying the magnetic field to the sample, thereby sequestering the cells; and
isolating the cells from the sample.

9. The method of claim 1, further comprising purifying the recovered nucleic acid to a purity sufficient for sperm STR profiles to be obtained that are suitable for genotyping.

10. The method of claim 1, wherein the sperm cells are selectively lysed in a sperm cell lysis buffer comprising DTT.

11. The method of claim 1, wherein the concentration of $MgCl_2$ is 30 mM to 260 mM.

12. The method of claim 1, wherein the DNase is 5 U or more per 100 µl.

13. A method for selectively recovering DNA from sperm cells in a sample containing mixed sperm cells and epithelial cells and a cell suspension medium comprising impurities, said impurities including contaminating residual DNA, the method comprising the steps of:
(i) introducing the sample onto a size exclusion filter;
(ii) washing the sample by mixing it with a first washing solution comprising from 20 mM to 300 mM $MgCl_2$ to form a washed sample, thereby disengaging or digesting residual DNA from the surface of the cells prior to introducing the sample onto the size exclusion filter;
(iii) isolating the mixed cells from the cell suspension medium in a first isolating step by sequestering the cells on the filter and allowing the cell suspension medium to form a filtrate;
(iv) washing the isolated mixed cells with a second washing solution comprising DNase followed by isolating the washed mixed cells from the second washing solution in a second isolating step, prior to said lysing step;
(v) lysing selectively the sperm cells;
(vi) recovering the DNA from the sperm cells.

14. The method of claim 13, wherein the DNase is 0.01 U to 50 U per 100 µl.

15. The method of claim 13, further comprising purifying the recovered nucleic acid to a purity sufficient for sperm STR profiled to be obtained that are suitable for genotyping.

16. A method for selectively recovering nucleic acid from sperm cells in a sample containing mixed sperm cells and epithelial cells and a cell suspension medium comprising impurities, said impurities including contaminating residual DNA, the method comprising the steps:
(i) washing the sample by mixing it with a first washing solution comprising from 20 mM to 300 mM $MgCl_2$ to form a first washed sample, thereby disengaging residual or digesting DNA from the surface of the cells prior to centrifuging the sample;
(ii) centrifuging the first washed sample to form a cell pellet and a supernatant containing the suspension medium, including any first washing solution, thereby sequestering the mixed cells from the suspension;
(iii) isolating the mixed cells from the supernatant in a first isolating step;
(iv) washing the isolated mixed cells with a second washing solution comprising DNase followed by centrifuging the washed mixed cells and second washing solution to form a pellet and a supernatant, thereby sequestering the washed cells from the suspension, and isolating the mixed washed cells from the supernatant, in a second isolating step, prior to said lysing step;
(v) lysing selectively the sperm cells;
(vi) recovering DNA from the sperm cells.

17. The method of claim 15, further comprising purifying the recovered nucleic acid to a purity sufficient for sperm STR profiled to be obtained that are suitable for genotyping.

* * * * *